US005863895A

United States Patent [19]
Benbow et al.

[11] Patent Number: 5,863,895
[45] Date of Patent: Jan. 26, 1999

[54] INHIBITOR OF CHROMOSOMAL DNA REPLICATION IN XENOPUS: THE TURHUTER PROTEIN

[75] Inventors: Robert M. Benbow, Bethesda, Md.; Jiyong Zhao, Charlestown, Mass.

[73] Assignee: Iowa State University Research Foundationv, Ames, Iowa

[21] Appl. No.: 525,877

[22] Filed: Sep. 8, 1995

Related U.S. Application Data

[63] Continuation-in-part of Ser. No. 302,608, Sep. 8, 1994, abandoned.

[51] Int. Cl.$^6$ ............................ A61K 38/16; C07K 14/46; C07K 1/16
[52] U.S. Cl. ............................ 514/12; 530/350; 530/413
[58] Field of Search .................................. 530/350, 413, 530/415, 416, 417; 514/12

[56] References Cited

PUBLICATIONS

R.M. Benbow et al., "DNA Unwinding and Strand Synthesis During Replication in *Xenopus laevis* Embryos" in *Advances in Applied Biotechnology Series, vol. 7, Gene Regulation and Aids*, 69–86 (1990).

R.M. Benbow et al., "Cytoplasmic Control of Nuclear DNA Synthesis During Early Development of *Xenopus laevis*: A Cell–Free Assay", *Proc. Natl. Acad. Sci. USA*, 72, 2437–2441 (Jun. 1975).

J.J. Blow et al., "Initiation of DNA Replication in Nuclei and Purified DNA by a Cell–Free Extract of Xenopus Eggs", *Cell*, 577–587 (Nov. 21, 1986).

J.J. Blow et al., "A role for the nuclear envelope in controlling DNA replication within the cell cycle", *Nature*, 332, 546–548 (Apr. 7, 1988).

J.J. Blow et al., "Replication of purified DNA in *Xenopus* egg extract is dependent on nuclear assembly", *J. Cell Sci.*, 95, 383–391 (1990).

J.J. Blow, "Preventing Re–replication of DNA in a Single Cell Cycle: Evidence for a Replication Licensing Factor", *J. Cell Biol.*, 122, 993–1002 (Sep. 1993).

M.M. Bradford, "A Rapid and Sensitive Method for the Quantitation of Microgram Quantities of Protein Utilizing the Principle of Protein–Dye Binding", *Anal. Biochem.*, 72, 248–254 (1976).

C.A. Casiano et al., "Autoantibodies to a novel cell cycle–regulated protein that accumulates in the nuclear matrix during S phase and is localized in the kinetochores and spindle midzone during mitosis", *J. Cell Science*, 106, 1045–1056 (1993).

R. Cortese et al., "Transition of tRNA genes in vivo: Single–stranded compared to double–stranded templates", *Proc. Natl. Acad. Sci. USA*, 77, 4147–4151 (Jul. 1980).

D. Coverley et al., "Regulation of Eukaryotic DNA Replication", *Annu. Rev. Biochem.*, 63, 745–776 (1994).

L.S. Cox et al., "Extracts from eggs and oocytes of *Xenopus laevis* differ in their capacities for nuclear assembly and DNA replication", *J. Cell Sci.*, 97, 177–184 (1990).

L.S. Cox, "DNA replication in cell–free extracts from *Xenopus* eggs is prevented by disrupting nuclear envelope function", *J. Cell Sci.*, 101, 43–53 (1992).

J.N. Dumont, "Oogenesis in *Xenopus laevis* (Daudin)", *J. Morph.*, 136, 153–179 (1972).

C.C. Ford et al., "DNA Synthesis in Oocytes and Eggs of *Xenopus laevis* Injected with DNA", *Developmental Biology*, 43, 189–199 (1975).

C.C. Ford et al., "A method for enucleating Oocytes of *Xenopus laevis*", *J. Embryol. exp. Morph.*, 37, 203–209 (1977).

A.M. Fox et al., "Intracellular Localization of DNA Polymerase Activities within Large Oocytes of the Frog, *Xenopus laevis*", *Developmental Biology*, 80, 79–95 (1980).

C.F. Graham et al., "Induction of DNA Synthesis by Frog Egg Cytoplasm", *Devlopmental Biology*, 14, 349–381 (1966).

J.B. Gurdon, "On the Origin and Persistence of a Cytoplasmic State Inducing Nuclear DNA Synthesis in Frogs' Eggs", *Proc. Natl. Sci. USA*, 58, 545–552 (Aug. 1967).

J.B. Gurdon et al., "Changes in somatic cell nuclei inserted into growing and maturing amphibian oocytes", *J. Embryol. exp. Morph.*, 20, 401–414 (Nov. 1968).

J.B. Gurdon et al., "The Appearance of Cytoplasmic DNA Polymerase Activity During the Maturation of Amphibian Oocytes into Eggs", *Exp. Cell.. Res.*, 55, 253–256 (1969).

O. Haccard et al., "Induction of Metaphase Arrest in Cleaving *Xenopus* Embryos by MAP Kinase", *Science*, 262, 1262–1265 (Nov. 19, 1993).

R.M. Harland et al., "Regulated Replication of DNA Microinjected into Eggs of Xenopus Laevis", *Cell*, 21, 761–771 (Oct. 1980).

S. Hiraga et al., "In vitro replication of recombinant plasmids carrying chromosomal segments of *Xenopus laevis*", *Proc. Natl. Acad. Sci. USA*, 79, 3697–3701 (Jun. 1982).

C.J. Hutchison et al., "Periodic DNA synthesis in cell–free extracts of Xenopus eggs", *EMBO J.*, 6, 2003–2010 (1987).

C.J. Hutchison et al., "The control of DNA replication in a cell–free extract that recapitulates a basic cell cycle in vitro", *Development*, 103, 553–566 (1988).

H.B. Kaiserman et al., "Characterization of a stable, major DNA polymerase or species devoid of DNA primase activity", *Nucl. Acids Res.*, 15, 10249–10265 (1987).

U.K. Laemmli, "Cleavage of Structural Proteins during the Assembly of the Head of Bacteriophage T4", *Nature*, 227, 680–685 (Aug. 15, 1970).

(List continued on next page.)

Primary Examiner—Robert A. Wax
Assistant Examiner—Kawai Lau
Attorney, Agent, or Firm—Mueting, Raasch Gebhardt & Schwappach, P.A.

[57] ABSTRACT

A composition is provided that inhibits DNA replication in activated cell-free extracts of Xenopus eggs, which is prepared by a process comprising subjecting homogenates of Xenopus ovaries to a series of chromatographic separations so as to isolate a purified fraction comprising a protein having a molecular weight of about 245 kDa.

5 Claims, 17 Drawing Sheets

OTHER PUBLICATIONS

M.J. Lohka et al., "Induction of Nuclear Envelope Breakdown, Chromosome Condensation, and Spindle Formation in Cell–Free Extracts", *J. Cell Biol.*, 101, 518–523 (Aug. 1985).

J. Maller et al., "Changes in Protein Phosphorylation Accompanying Maturation of *Xenopus laevis* Oocytes", *Developmental Biology*, 58, 295–312 (1977).

J.L. Maller et al., "Progesterone–stimulated Meiotic Cell Division in Xenopus Oocytes", *J. Biol. Chem.* 252, 1712–1718 (Mar. 10, 1977).

J. Marx, "How Cells Cycle Toward Cancer", *Science*, 263, 319–321 (Jan. 21, 1994).

J. Messing, "New M13 Vectors for Cloning", *Methods Enzymol.*, 101, 20–79 (1983).

A.W. Murray, "Cell Cycle Extracts", *Methods in Cell Biol.*, 36, 581–605 (1991).

J. Newport, "Nuclear Reconstitution In Vitro: Stages of Assembly around Protein–Free DNA", *Cell,* 48, 205 (Jan. 30, 1987).

I. Ruberti et al., "Large Scale Isolation of Nuclei from Oocytes of *Xenopus laevis*", *Anal. Biochem.*, 180, 177–180 (1989).

J. Sambrook et al. in *Molecular Cloning (A Laboratory Manual)*, Cold Spring Harbor Laboratory Press: Cold Spring Harbor, NY (1989). (Title Page, Copyright Page, and Contents Pages (pp. v–xxxii)).

M.A. Sheehan et al., "Steps in the Assembly of Replication–competent Nuclei in a Cell–free System from Xenopus Eggs", *J. Cell Biol.*, 106, 1–12 (Jan. 1988).

C. Smith et al., "Preliminary Characterisation of Inhibitors of DNA Polymerase Isolated from *Xenopus laevis* Early Embryos", *Biochim. Biophys. Acta*, 741, 109–115 (1983).

L.D. Smith in *The Biochemistry of Animal Development, vol. III*; R. Weber, Ed.; Academic Press: New York; pp. 1–46 (1975).

J. Travis, "Looking for Cancer in Nuclear Matrix Proteins", *Science*, 259, 1258 (Feb. 26, 1993).

L–H. Tsai et al., "The cdk2 kinase is required for the G1–to–S transition in mammalian cells", *Oncogene*, 8, 1593–1602 (1993).

S. van den Heuvel et al., "Distinct Roles for Cyclin–Dependent Kinases in Cell Cycle Control", *Science*, 262, 2050–2054 (Dec. 24,1993).

A.H. Wyllie et al., "Selective DNA Conservation and Chromatin Assembly after Injection of SV40 DNA into Xenopus Oocytes", *Development Biology*, 64, 178–188 (1978).

J. Zhao et al., "An Inhibitor of DNA Topoisomerase I from *Xenopus laevis* Ovaries", *Biochemistry*, 32, 10622–10628 (1993).

J. Zhao et al., "Negative Control of Chromosomal DNA Replication in Cell–free Extracts of *Xenopus laevis* Eggs by Factors from *Xenopus laevis* Ovaries", Abstract of Papers, *Eukaryotic DNA Replication Meeting*, Sep. 8–12, 1993; Cold Spring Harbor Laboratory: Cold Spring Harbor, NY (1993).

J. Zhao et al., "Inhibition of DNA Replication in Cell–Free Extracts of *Xenopus laevis* Eggs by Factors from *Xenopus laevis* Ovaries", Abstract of Papers, 33rd Annual Meeting of the American Society for Cell Biology, New Orleans, LA (Dec. 11–15, 1993); printed in *Supplement to Molecular Biology of the Cell*, 4, 17a, Abstract No. 91 (Oct. 1993).

J. Zhao et al., "Inhibition of DNA Replication in Cell–Free Extracts of *Xenopus laevis* Eggs by Extracts of *Xenopus laevis* Oocytes", *Developmental Biology*, 164, 52–62 (1994).

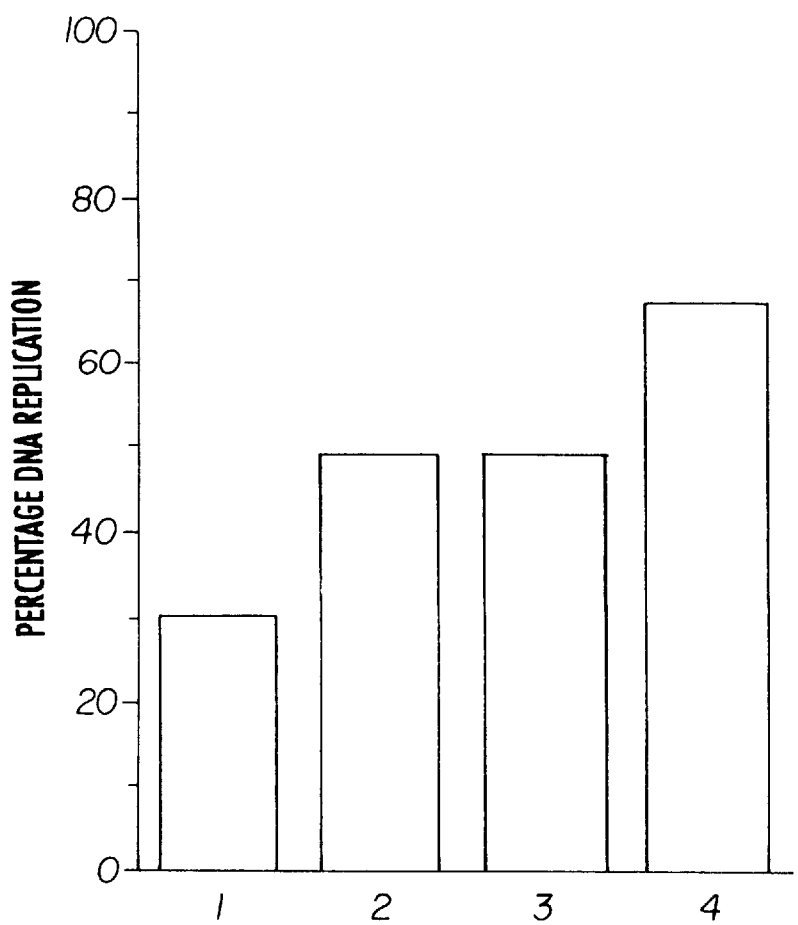

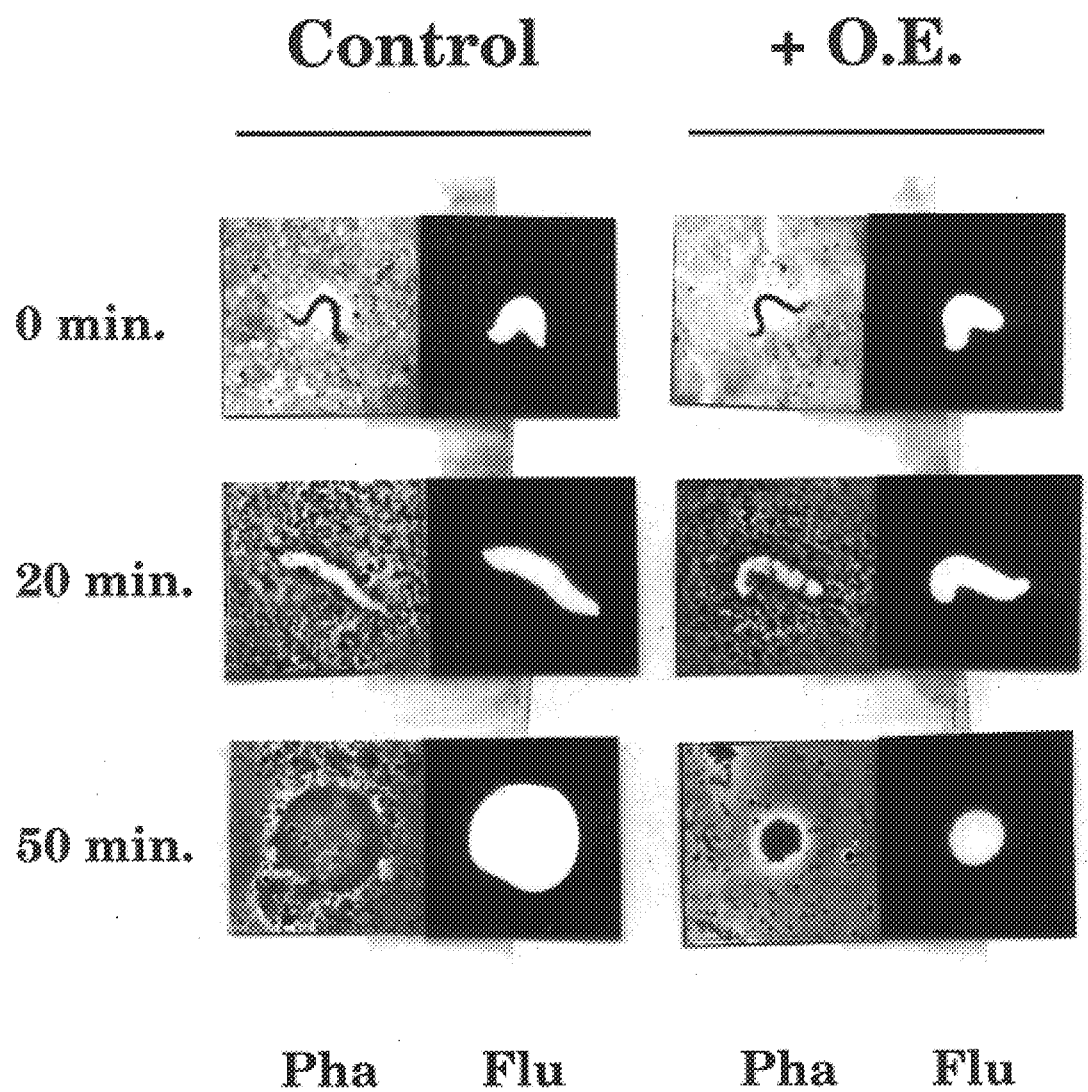

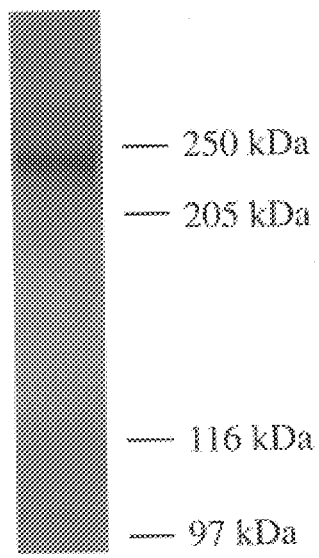
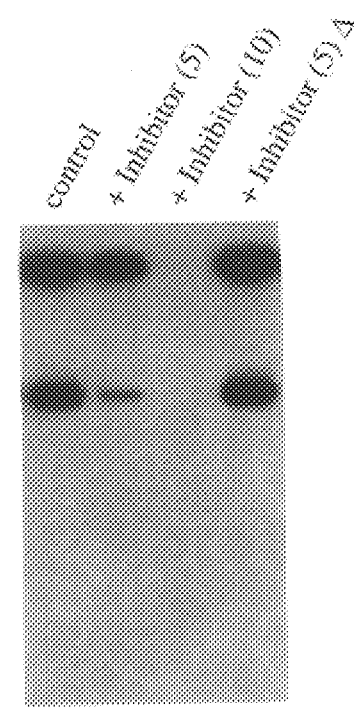
Fig. 10A
Fig. 10B

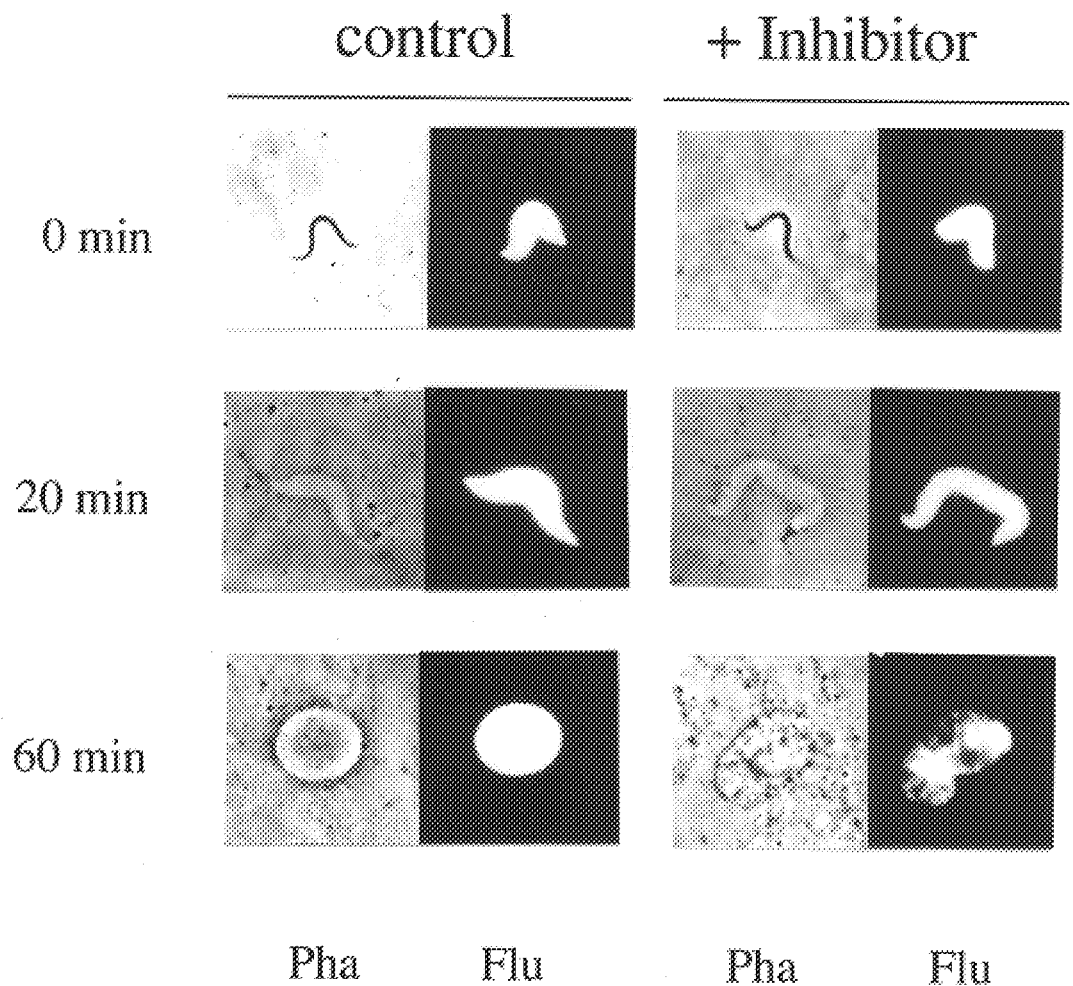

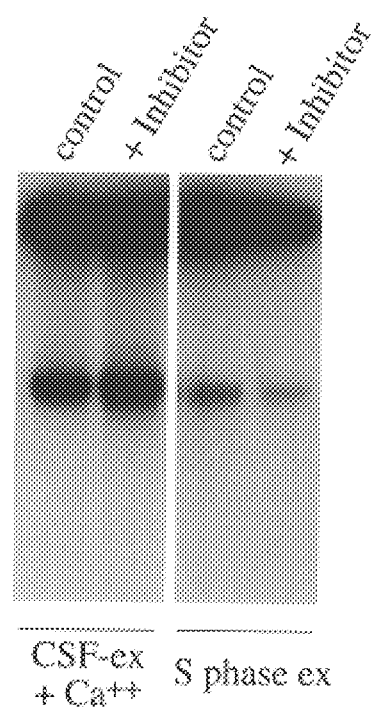

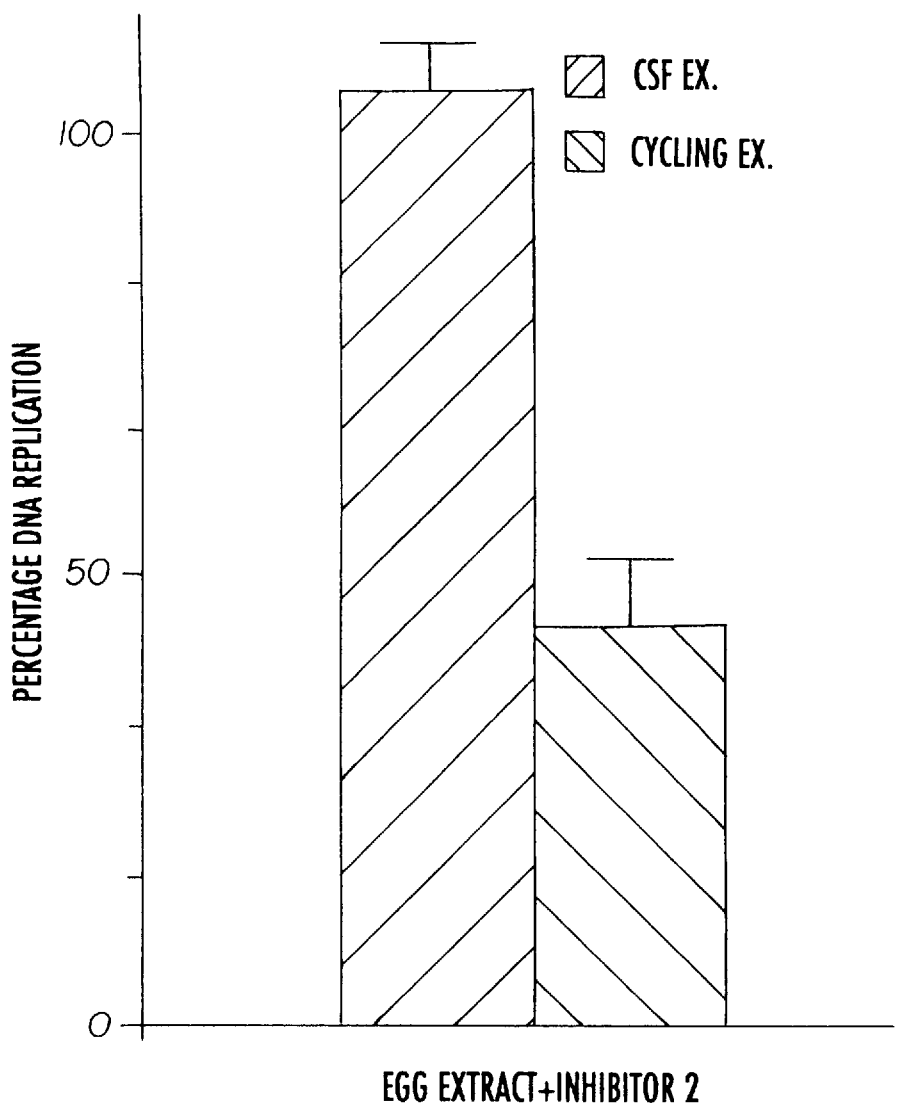

INHIBITOR OF CHROMOSOMAL DNA REPLICATION IN XENOPUS: THE TURHUTER PROTEIN

CROSS-REFERENCE TO RELATED APPLICATIONS

The present invention is a Continuation-In-Part of U.S. patent application Ser. No. 08/302,608, filed on Sep. 8, 1994 now abandoned, the disclosure of which is incorporated herein by reference.

BACKGROUND OF THE INVENTION

Chromosomal DNA replication is one of the most fundamental biological processes in all metazoan organisms. Typically, every chromosome is faithfully replicated once and only once during each cell division cycle. Rather astonishingly, the mechanism of chromosomal DNA replication in metazoa remains largely unknown 40 years after the discovery of the structure of DNA. For example, it is not known how metazoan cells "decide" whether and when to begin replicating their DNA in preparation for cell division.

Inquiries into the mechanisms of chromosomal DNA replication are significant to most health-related research. Efforts to understand the mechanics of eukaryotic DNA replication and cell division during mitosis and meiosis are important to the development of new methods of detection and treatment of diseases characterized by rapid cell proliferation, such as cancer. In cancer, there is "accumulating evidence that derangements in the cell cycle machinery may contribute to the uncontrolled cell growth characteristic of a tumor" (Marx, *Science*, 263, 319–321 (1994)).

Chromosomal origins of DNA replication in higher eukaryotes differ significantly from the those of *E. coli* (ori C) and the tumor virus, SV40 (ori sequence). Chromosomal DNA replication events in Xenopus (frog) cell-free egg extracts and embryos provide a model system for characterization of chromosomal DNA replication in metazoan organisms, such as humans. Xenopus nuclei replicate only in S phase. Studies of DNA replication in cell-free extracts of Xenopus embryos and eggs have indicated the presence of positive initiation factors in Xenopus embryos and activated eggs that "turn on" DNA replication (R. M. Benbow et al., *Proc. Natl. Acad. Sci. USA*, 72, 2437–2441 (1975); J. J. Blow et al., *Nature*, 332, 546–548 (1988); J. J. Blow, *J. Cell Biol.*, 122, 993–1002 (1993)). These initiation factors, which have yet to be purified and characterized, are prevented from entering the $G_2$ nucleus by the nuclear membrane.

Oocytes of *Xenopus laevis*, as well as many other animal species, are arrested at the $G_2$/prophase of the first meiotic division for a prolonged time. Full-grown stage VI oocytes or cell-free extracts of oocytes do not support replication of either nuclei or purified double-stranded DNA molecules (C. C. Ford et al., *Dev. Biol*, 43, 189–199 (1975); L. S. Cox et al., *J. Cell Sci.*, 97, 177–184 (1990)). Maturation of oocytes to eggs results in appearance of the capacity to replicate double-stranded DNA templates.

Although the molecular events that occur during oocyte maturation have been extensively studied (see, for example, L. D. Smith in *The Biochemistry of Animal Development;* R. Weber, Ed.; Vol. 3, pp. 1–46 (1975)), it is still not clear how the change in DNA replication capacity (absent in oocytes, copious in eggs) is regulated. It is known that changes in nuclear activity are induced by certain cytoplasmic factors (C. F. Graham et al., *Dev. Biol.*, 14, 349–381 (1966); J. B. Gurdon, *J. Embryol. Exp. Morph.*, 20, 401–414 (1968); R. M. Benbow et al., *Proc. Natl. Acad. Sci. USA*, 72, 2437–2441 (1975)). It has been suggested that the inability of oocytes to support DNA replication is either due to the absence of positive initiation factors in oocytes (which are present in eggs), or to the presence of one or more inhibitors of DNA polymerases or other replication enzymes (J. B. Gurdon, *Proc. Natl. Acad. Sci.*, 58, 545–552 (1967); J. B. Gurdon et al., *Exp. Cell Res.*, 55, 253–256 (1969); R. M. Benbow et al., *Proc. Natl. Acad. Sci. USA*, 72, 2437–2441 (1975)).

Neither of these explanations is adequate. If oocytes were lacking positive initiators found in eggs, then combining oocyte extracts with cell-free egg extracts would stimulate DNA replication. Instead, DNA replication in egg extracts is decreased or even abolished when oocyte extracts are added thereto (J. Zhao et al., *Biochemistry*, 32, 10622–10628 (1993); R. M. Benbow et al., *Adv. Appl. Biotechnol.*, 7, 69–86 (1990)). Nor do the presence in oocytes of polymerase inhibitors or inhibitors of other catalytic enzymes (A. M. Fox et al., *Dev. Biol.*, 80, 79–95 (1980); C. Smith et al., *Biochim. Biophys. Acta*, 741, 109–115 (1983)) explain the failure of oocytes to support DNA replication, because inhibitors of this type have also been reported in Xenopus eggs (C. Smith et al., *Biochim. Biophys. Acta*, 741, 109–115 (1983)). To further confound explanations for the general inability of oocytes to support DNA replication and the observed inhibitory effect exerted by oocyte extracts on DNA replication in egg extracts, complementary strand DNA synthesis is observed on single-stranded DNA templates microinjected into Xenopus oocyte nuclei (C. C. Ford et al., *Dev. Biol.*, 43, 189–199 (1975); R. Cortese et al., *Proc. Natl. Acad. Sci. USA*, 77, 4147–4151 (1980)), suggesting that in oocytes the enzymatic steps in chain elongation and termination are otherwise operative.

Some other factor, then, possibly one that exerts a direct negative effect on the control of DNA replication, must be involved in the failure of oocytes to support DNA replication. Isolation, identification and characterization of this factor is needed to advance our knowledge of cell-cycle control of eukaryotic DNA replication and our understanding and treatment of diseases characterized by malfunctions in the cell-cycle control mechanism, such as cancer. Potentially, this factor could be one that exercises a negative gateway control over the entire series of events that constitutes DNA replication in eukaryotes.

SUMMARY OF THE INVENTION

A factor was discovered in Xenopus oocytes that inhibits DNA replication in Xenopus egg extracts, possibly by blocking initiation of replication, an important gateway for negative regulation of DNA replication. Accordingly, the inventors refer to the protein as the "Tütrhüter (gatekeeper) protein."

The present invention provides a composition that contains a protein derived from the ovaries of *Xenopus laevis*. This protein is involved in the inhibition of DNA replication in oocytes or oocyte extracts. Preferably, the protein inhibits replication of double stranded DNA templates and Xenopus sperm nuclei. The composition is conveniently prepared from homogenates of Xenopus ovaries using a purification process that involves a series of chromatographic separations. A preferred embodiment of the invention involves the use of chromatographic resins made of diethylaminoethyl-cellulose, phosphocellulose, hydroxyapatite-agarose, Affi-gel Blue gel (a hydrophobic resin), and heparin-agarose in the preparation of the composition. The size of the protein is conveniently measured using sodium dodecyl sulfatepolyacrylamide gel electrophoresis and is about 245 kiloDaltons (kDa).

BRIEF DESCRIPTION OF THE DRAWINGS

FIG. 2. Inhibition of DNA replication in different cell-free egg extracts by an oocyte extract. Sperm nuclei were incubated in four different egg extracts in the presence of aliquots of the same oocyte extract for 50 minutes.

FIG. 3. Inhibition of replication of plasmid DNA templates in cell-free egg extracts by an extract of oocytes. An autoradiogram of an agarose gel of pXY65 DNA synthesized in egg extracts in the presence of extraction buffer (Control) or oocyte extract (+O.E.) for 90 minutes is shown. The positions of supercoiled (form I) and relaxed (form Ir) monomeric pXY65 DNA are indicated.

FIG. 8. Effect of oocyte extracts on formation of nuclei in cell-free egg extracts. Sperm nuclei were incubated in egg extracts in the presence of 10 µl extraction buffer (Control) or 10 µl oocyte extract (+O.E.). Samples were taken and mixed with equal volumes of fix and stain solution at 0 minutes, 10 minutes and 50 minutes, as indicated, for phase-contrast (Pha) and fluorescence (Flu) microscopy. Scale bar, 20 µm.

FIG. 11. Effect of the purified inhibitor on nuclear formation in Xenopus egg extracts. Xenopus sperm nuclei were incubated in 35 µl egg extracts in the presence of 10 µl control buffer (Control) or 10 µl purified inhibitor (+Inhibitor 2). Samples were examined at 0 minutes, 20 minutes, and 60 minutes, as indicated, for phase-contrast (Pha) and fluorescence (Flu) microscopy.

FIG. 12. Cell-cycle dependent inhibition of DNA replication by p245. (A) Xenopus sperm nuclei, together with 5 µl control buffer (Control) or the most purified fraction (Inhibitor), as indicated, were added to 35 µl metaphase-arrested egg extracts (i.e., cytostatic factor (CSF) extract) or S phase extracts at 0° C. Then CaCl$_2$ (1.5 mM) was added to inactivate CSF. Metaphase extracts (CSF extracts) were prepared according to the procedure of M. J. Lohka et al., *J. Cell Biol.*, 101, 518 (1985) and A. W. Murray, *Methods in Cell Biol.*, 36, 581 (1991); S phase extracts were prepared as described below in Example I according to the procedure of Hutchison et al. (*Development*, 103, 553–566 (1988)); and the control buffer was the buffer used for the most purified fraction, which is Buffer F described below in Example II. Reactions were carried out at 23° C. for 60 minutes. The reaction products were analyzed by agarose gel electrophoresis and autoradiography. (B) DNA synthesis shown in the reactions shown in (A) was quantitated and percentage DNA synthesis was calculated. As a comparison, percentage DNA synthesis in cycling extracts is also shown.

DETAILED DESCRIPTION OF THE INVENTION

Figure 1A:
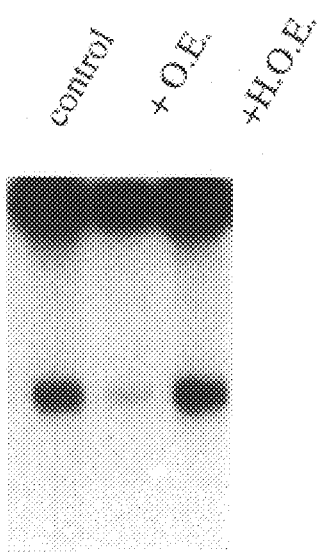
FIG. 1. Inhibition of replication of Xenopus sperm nuclei in cell-free extracts of Xenopus eggs by extracts of Xenopus oocytes. (A) An autoradiogram of an agarose gel after electrophoresis of DNA synthesized in vitro. Sperm nuclei were incubated in egg extracts in the presence of extraction buffer (Control), oocyte extract (+O.E.) or heat treated (80° C., 10 minutes) oocyte extract (+H.O.E.) for 60 minutes. Typically two bands were observed for sperm nuclear DNA on agarose gels. The lower band represented DNA that migrated into the gels; the upper band, that did not migrate into the gels, was DNA presumably complexed with proteins. The relative intensity of the two bands depends on the extent of proteinase K treatment. (B) Quantification of inhibition of DNA replication in egg extracts by oocyte extracts. Sperm nuclei were incubated in four different egg extracts (1, 2, 3, 4) in the presence of four different oocyte extracts for 60 minutes. (C) Concentration dependence of inhibition of DNA replication in egg extracts. Sperm nuclei were incubated in egg extracts in the presence of the indicated amount of oocyte extract for 60 minutes.

The present invention provides a composition containing a protein that is involved in the regulation of chromosomal DNA replication in Xenopus immature oocytes. An immature oocyte is a Stage I to Stage V oocyte (Dumont's stages of oogenesis, J. N. Dumont, *J. Morphol.*, 136, 153–180 (1972)). Preferably, the protein suppresses or inhibits DNA replication. The protein has a molecular weight of about 245 kDa in size, and may preferably be isolated from Xenopus ovaries or oocytes. Although the inventors do not wish to be held to any particular theory, it is believed that this protein acts as a negative regulator of DNA replication. By "negative regulator" it is meant that the protein blocks the action of one or more positive regulatory molecules that control the initiation of DNA replication, rather than acts as an inhibitor of a DNA polymerase or other enzyme needed for DNA synthesis. The expression level of the protein provided by the invention is under cell cycle control.

The protein provided by the present invention was discovered in cell-free extracts of Xenopus oocytes. Cell-free extracts of activated *Xenopus laevis* eggs support replication of Xenopus sperm nuclei and purified double-stranded plasmid DNA templates, whereas cell-free extracts of Xenopus oocytes do not. The activated egg extract behaves much like the intact egg. Eggs may be activated by, for example, treatment with calcium ionophores. When cell-free extracts of Xenopus oocytes are added to activated cell-free extracts of Xenopus eggs, replication of Xenopus sperm nuclei and double-stranded plasmid DNA templates is inhibited.

The protein responsible for the DNA replication inhibition activity present in cell-free extracts of Xenopus oocytes may be isolated or purified using a combination of purification procedures known in the art. During purification, the presence or absence of DNA replication inhibition activity in any given purification fraction can be conveniently used as an assay to determine a likely location of the protein.

Procedures used to isolate and purify the inhibition activity from Xenopus ovaries described above may include tissue homogenation, centrifugation, chromatography, dialysis, concentration, buffer exchange, precipitation, gel electrophoresis, or any other laboratory method useful in separating the protein of the invention from other components of the Xenopus ovary. Preferably, the protein is isolated from homogenized Xenopus ovaries using a series of chromatographic separations. More preferably, the purification procedure used to isolate the protein of the present invention from homogenized Xenopus ovaries involves a combination of chromatographic separations and gel electrophoresis steps. Most preferably, the purification procedure consists of a scheme involving the following steps: subjecting the tissue homogenate to centrifugation, DEAE-cellulose chromatography, concentration and buffer exchange, phosphocellulose chromatography, concentration and buffer exchange, hydroxyapatite agarose chromatography, concentration, Affi-gel Blue gel chromatography, concentration, hydroxyapatite agarose chromatography, concentration and buffer exchange, Heparin agarose chromatography, concentration and buffer exchange, and gel electrophoresis. The purification procedure may be carried out by beginning with homogenation and high-speed centrifugation of Xenopus ovaries; followed by chromatographic separation of the components of the supernatant on a DEAE-cellulose column in an appropriate buffer solution, using a salt gradient; followed by concentration and desalting of the fraction containing the inhibition activity; followed by chromatographic separation on a phosphocellulose column using an appropriate buffer solution; followed by concentration and buffer exchange of the fraction containing the inhibition activity; followed by chromatographic separation on a hydroxyapatite-agarose column using an appropriate buffer solution; followed by concentration of the fraction containing the inhibition activity; followed by chromatographic separation on an Affi-gel Blue gel column using an appropriate buffer solution; followed by concentration of the fraction containing the inhibition activity; followed by chromatographic separation on an hydroxyapatite-agarose column using an appropriate buffer solution; followed by concentration and buffer exchange of the fraction containing the inhibition activity; followed by chromatographic separation on a Heparin-agarose column using an appropriate buffer solution and a salt gradient; followed by concentration, desalting, and buffer exchange of the fraction containing the inhibition activity; followed by sodium dodecyl sulfate-polyacrylamide gel electrophoresis (SDS-PAGE) to isolate the protein; followed by electroelution and renaturation of the protein.

The protein purified according to the method described herein, referred to as p245, is useful as a regulator of DNA replication. That is, it inhibits chromosomal DNA replication. Generally it is believed to be a negative regulator. This is supported by the fact that it does not block DNA synthesis on double-stranded plasmid DNA templates nor complementary strand synthesis on single-strand DNA templates in egg extracts, which suggests that p245 inhibits initiation of DNA replication rather than chain elongation. Furthermore, it does not affect plasmid pBR322 DNA replication, although it does alter the morphology of nuclei formed in Xenopus egg extracts. Also, it is inactive in metaphase or during M to S phase transition in Xenopus egg extracts.

The invention has been described with reference to various specific and preferred embodiments and will be further described by reference to the following detailed examples. It is understood, however, that there are many extensions, variations, and modifications on the basic theme of the present invention beyond that shown in the examples and detailed description, which are within the spirit and scope of the present invention.

EXPERIMENTAL EXAMPLES

Example 1

Inhibition of DNA Replication in Xenopus Egg Extracts Treated with Xenopus Oocyte Extracts A. Materials Demembranated Xenopus sperm nuclei were prepared essentially as described by J. J. Blow et al., *Cell*, 47, 577–587 (1986). Plasmid pXY65 DNA (S. Hiraga et al., *Proc. Natl. Acad. Sci. USA*, 79, 3697–3701 (1982)) was prepared by the alkaline lysis method (J. Sambrook et al. in *Molecular Cloning (A Laboratory Manual)*, Cold Spring Harbor Laboratory Press: Cold Spring Harbor, N.Y. (1989)). Single-stranded M13 DNA was isolated by the procedure of J. Messing (*Methods Enzymol.*, 101, 20–79 (1983)) and further purified by CsCl density gradient centrifugation (J. Sambrook et al. in *Molecular Cloning (A Laboratory Manual)*, Cold Spring Harbor Laboratory Press: Cold Spring Harbor, N.Y. (1989)).

Xenopus egg extracts were prepared as described by Hutchison et al. (*Development*, 103, 553–566 (1988)) and used within 1 hour of preparation. It should be emphasized that eggs are activated by this procedure. "Activation" is a term specific to developmental biology that refers to all the collective reactions that characterize egg metabolism. Activation sets into motion a preprogrammed set of metabolic events, including the release of calcium, G protein stimulation, blocks to polyspermy, increases in intracellular pH, stimulation of DNA and protein synthesis, and cytoplasmic movements of morphogenetic material. Activation of eggs generally occur in response to a variety of stimuli, such as exposure to electric currents, fertilization by sperm, prick by a dirty needle, or treatment with a calcium ionophore.

To prepare Xenopus oocyte extracts, ovaries were removed from decapitated mature female frogs and treated with 1.5–2% collagenase (Type II, Sigma Chemical Company, St. Louis, Mo.) in modified Barth solution ("MBS," C. C. Ford et al., *J. Embryol. Exp. Morph.*, 37, 203–209 (1977)) at room temperature for 2–4 hours to disperse oocytes. Stage VI oocytes (J. N. Dumont, *J. Morph.*, 136, 153–180 (1972)) were isolated and washed sequentially with MBS, deionized water, and cold extraction buffer (30 mM HOPES, pH 7.5, 60 mM KCl, 5 mM $MgCl_2$, 2 mM β-mercaptoethanol, 3 μg/ml leupeptin) (Sigma Chemical Co., St. Louis, Mo.). Oocytes were packed into a cooled, tight-fitting ground glass homogenizer (PYREX) and excess buffer was removed. Oocytes were homogenized by 10–15 up-and-down strokes. The homogenate was centrifuged at 16,000×g for 5 minutes at 4° C. The soluble fraction between the lipid cap and yolk pellet was collected. Cytochalasin B (50 μg/ml), leupeptin (6 μg/ml) and aprotinin (80 Kallekrein units/ml) (Sigma Chemical Company, St. Louis, Mo.) were added, and the oocyte extract was centrifuged for another 5 minutes. The soluble fraction was collected and the volume was adjusted with cold extraction buffer so that 1 μl extract would be equivalent to 1 oocyte. The extracts were stored in aliquots at −75° C. The protein concentration of the oocyte extracts, measured by the method of M. M. Bradford (*Anal. Biochem.*, 72, 248–254 (1976)) using bovine plasma γ-globulin (Bio-Rad, Hercules, Calif.) as a standard, ranged from 43 to 47 mg/ml.

Preparation of extracts from mature oocytes was similar to preparation of extracts from immature oocytes. Two methods were employed to mature oocytes in vitro. In the first method, stage VI oocytes were induced to mature in vitro using progesterone as described by J. L. Maller et al., *J. Biol. Chem.*, 252, 1712–1718 (1977), except that MBS (C. C. Ford et al.,*J. Embryol. Exp. Morph.*, 37, 203–209 (1977)) was used in place of OR2 solution. The second method used high pH to induce oocyte maturation. Xenopus ovaries were washed with a high pH solution ("HMB solution," 10 mM Tris base, 88 mM NaCl, 1 mM KCl, 0.33 mM $Ca(NO_3)_2$, 0.41 mM $CaCl_2$, 0.82 mM $MgSO_4$, 2.4 mM $NaHCO_3$, pH 9.0), then incubated with 1.5% collagenase (Type II, Sigma Chemical Company, St. Louis, Mo.) in HMB solution at room temperature for 3–5 hours. Stage VI oocytes were isolated, washed with HMB solution, then incubated in HMB solution. At about 6.5 hours (from the beginning of treatment with collagenase), oocytes began to mature, judged by the appearance of white spots at animal poles (L. D. Smith in *The Biochemistry of Animal Development;* R. Weber, Ed.; Vol. 3; pp. 1–46 (1975); Maller et al., *J. Biol. Chem.*, 252, 1712–1718 (1977)). Matured oocytes were incubated in MBS or HMB solution for another 2–4 hours before preparation of the extracts.

Xenopus oocyte nuclei were isolated from stage V and VI oocytes according to the procedure described by I. Ruberti et al. (*Anal. Biochem.*, 180, 177–180 (1989)), except that buffers C, J, and lysis medium were changed as follows: buffer C: 20 mM HOPES, pH 7.5, 50 mM KCl, 5 mM $MgCl_2$, 1 mM dithiothreitol (DTT), 0.1 mM spermidine, 0.03 mM spermine, 5% (v/v) glycerol; buffer J: 20 mM HOPES, pH 7.5, 50 mM KCl, 5 mM $MgCl_2$, 1 mM DTT, 0.1 mM spermidine, 0.03 mM spermine, 10% (v/v) glycerol; lysis medium: HOPES, pH 7.4, 70 mM $NH_4Cl$, 7 mM $MgCl_2$, 0.1 mM EDTA, 2.5 mM DTT, 10 mM 0.2% Nonidet-P-40 (Sigma Chemical Company, St. Louis, Mo.).

Isolated Xenopus oocyte nuclei were disrupted with a pipette fitted with a 10–100 ml tip and homogenized in a glass homogenizer (PYREX). Aprotinin, leupeptin, pepstatin A and phenylmethyl-sulfonyl fluoride (PMSF) (Sigma Chemical Company, St. Louis, Mo.) were added to the homogenate at a final concentration of 80 Kallekrein units/ml, 10 μg/ml, 10 μg/ml and 0.2 mM, respectively, and the homogenate was centrifuged at 16,000×g for 5 minutes at 4° C. Soluble extracts were collected and stored in aliquots at −75° C. The final protein concentration of each of the nuclear extracts was 7.6 mg/ml.

B. Methods

1. In vitro DNA Replication Assay

DNA replication in cell-free egg extracts was carried out based on the method of Hutchison et al., (*EMBO J.*, 6, 2003–2010 (1987) and Development, 103, 553–566 (1988)). The reaction mixture contained 35 μl egg extract, $1.5 \times 10^4$ demembranated Xenopus sperm nuclei or 200 ng pXY65 DNA or 100 ng single-stranded M13mp18 DNA, 2 µCi [α-$^{32}$P]dATP and, unless otherwise specified, 5 µl oocyte extract or 5 µl oocyte nuclear extract, or 5 µl extraction buffer (control) as indicated. Assays were carried out at 23° C. for the indicated time and terminated with stop solution (Hutchison et al., *EMBO J.*, 6, 2003–2010 (1987)). Samples were treated with proteinase K (0.5 mg/ml, 1–2 hour at 37° C.) and electrophoresed on 0.8% agarose gels. After electrophoresis, gels were dried under vacuum and radioactivity was quantified using a Molecular Dynamics PhosphorImager (Sunnyvale, Calif.). DNA replication was measured by incorporation of [$^{32}$P]dAMP (duPont, Wilmington, Del.). Incorporation in control assays (egg extracts plus extraction buffer) was defined as 100% replication. Assays were carried out in duplicate.

2. Time Course of DNA Replication and Inhibition in Egg Extracts

Reaction mixtures contained 17.5 µl egg extract, 50 µg/ml cycloheximide, 6.7×10$^3$ Xenopus sperm nuclei, 2.5 µl extraction buffer or 2.5 µl oocyte extract and 1 µCi [α-$^{32}$P] dATP. The protein synthesis inhibitor, cycloheximide, was added to arrest the egg extracts in S phase, so that DNA replication in only a single cell cycle was measured (Hutchison et al., *EMBO J.*, 6, 2003–2010 (1987); Hutchison et al., *Development*, 103, 553–566 (1988)). Reactions were carried out at 23° C. for the indicated time and terminated with stop solution (Hutchison et al., *Development*, 103, 553–566 (1988)). Samples were treated with proteinase K before electrophoresis on 0.8% agarose gels. Radioactivity on dried gels was measured as described above. For the quantification of DNA synthesized in the egg extract, radioactivity on dried gels was determined in Scintiverse (Fisher) in an LKB 1218 Rackbeta scintillation counter. The amounts of DNA synthesized were calculated by assuming that dATP pool in egg extracts was 50 µM (J. J. Blow et al., *Cell*, 47, 577–587 (1986)). Inhibition of DNA replication (percentage DNA replication) was calculated using incorporation of [$^{32}$P]dAMP in control assays (egg extract plus buffer) at each corresponding time as 100% replication.

3. Quantification of Template DNA After Incubation in Egg Extracts

Two methods were used to quantify plasmid template DNA after incubation in egg extracts.

Method 1: [$^3$H]-labeled pXY65 DNA prepared as described by Zhao and Benbow (*Biochemistry*, 32, 10622–10628, (1993)) was incubated in egg extracts in the presence of oocyte extract or an equal volume of extraction buffer (Control). Reactions were stopped at 90 minutes and treated with proteinase K as described above. Samples were separated on a 0.7% agarose gel by electrophoresis and DNA was transferred to a nitrocellulose membrane (Schleicher & Schuell, Keene, N.H.) by Southern blotting (J. Sambrook et al. in *Molecular Cloning: A Laboratory Manual*), Cold Spring Harbor Laboratory Press: Cold Spring Harbor, N.Y. (1989)). After transfer, the membrane was washed with 2× SSC (0.3M NaCl, 0.03M sodium citrate, pH 7.0) and dried at room temperature. The radioactivity on membrane slices was quantified in Scintiverse (Fisher, Pittsburgh, Pa.) as described above. The percentage template DNA remaining after incubation in egg extracts was calculated relative to the amount of template DNA in egg extracts plus control buffer.

Method 2: [$^3$H]-labeled pXY65 DNA was incubated in egg extracts and treated with proteinase K. DNA in each sample was precipitated with 5% trichloroacetic acid, and acid-insoluble [$^3$H]-DNA was collected onto Whatman 934-AH filters (Hillstrom, Oreg.). The filters were dried under an infrared lamp, and radioactivity on the filters was quantified. The percentage of template DNA remaining after incubation was calculated as above.

4. Visualization of Nuclei

Samples were mixed with equal volumes of a solution of 20 mM HOPES, pH 7.5, 100 mM KCl, 5 mM MgCl$_2$, 3.7% formaldehyde, 10% (v/v) glycerol and 1.5 µg/ml Hoechst 33258 (Sigma Chemical Co., St. Louis, Mo.) on glass slides, covered with coverslips and examined under an Olympus BHS microscope (Lake Success, N.Y.).

C. Results

Figure 1B:
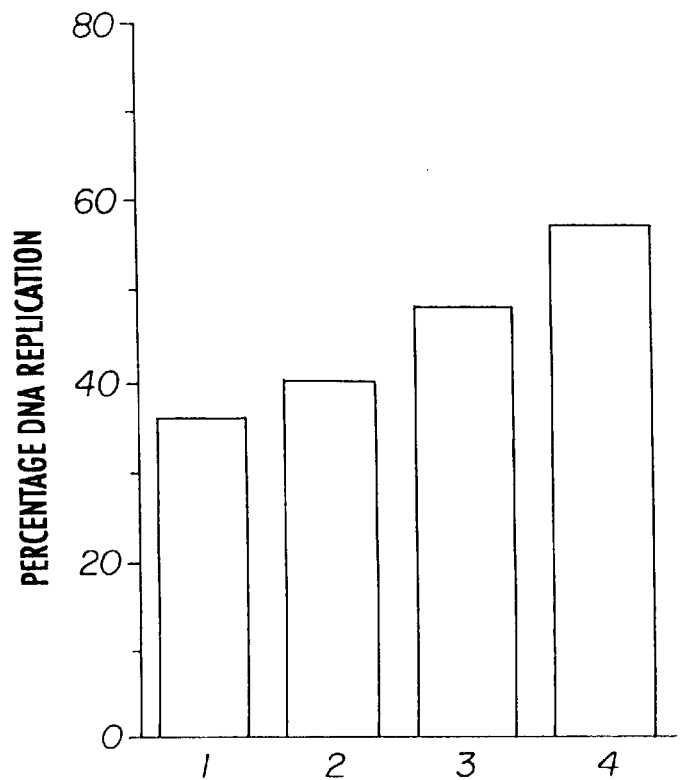
Figure 1C:
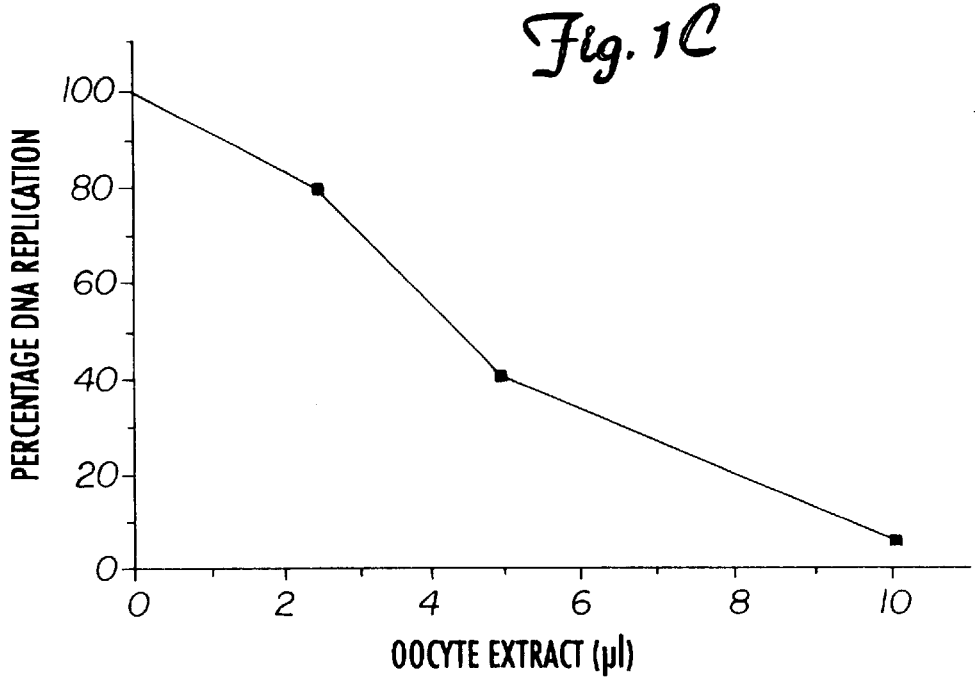

1. Replication of Xenopus Sperm Nuclei and Plasmid DNA in Xenopus Egg Extracts was Inhibited by Extracts of Xenopus Oocytes At the outset it was not known whether the inability of Xenopus oocytes to replicate chromosomal or microinjected DNA is due to the absence of essential positive activating factors or due instead to the presence of inhibitory factors. To resolve this question, extracts of Xenopus eggs were treated with stage VI extracts of Xenopus oocytes. If the inability of oocytes to replicate DNA is due to the absence of a positive factor, replication in egg extracts would not be diminished and might even be enhanced by addition of extracts of oocytes. Alternatively, if there were a dominant inhibitor of DNA replication present in oocytes, replication in egg extracts might be inhibited or even abolished by addition of oocyte extracts. As shown in FIG. 1, addition of extracts of stage VI Xenopus oocytes to extracts of Xenopus eggs inhibited replication of Xenopus sperm nuclear DNA in egg extracts. Over 10 preparations of oocyte extracts have been tested with more than 20 different preparations of egg extracts. In all experiments, addition of oocyte extracts resulted in inhibition of DNA replication in egg extracts. Representative results from these experiments are shown in FIG. 1B. Inhibition of DNA replication in egg extracts by oocyte extracts was heat sensitive (FIG. 1A) and dependent on the concentration of oocyte extracts (FIG. 1C). The extent of inhibition was variable in different preparations of egg extracts (FIG. 2). Replication of plasmid DNA in cell-free egg extracts was similarly inhibited by addition of oocyte extracts (FIG. 3).

The oocyte extracts used in this study were prepared by homogenization to ensure that the germinal vesicles were disrupted so that the contents of the nucleus would be in the extract. Inhibition of DNA replication by oocyte extracts, however, did not depend on homogenization, since addition of an oocyte extract prepared by low speed centrifugation (16,000×g, 10 minutes) also resulted in inhibition equivalent to that observed above.

Figure 4:
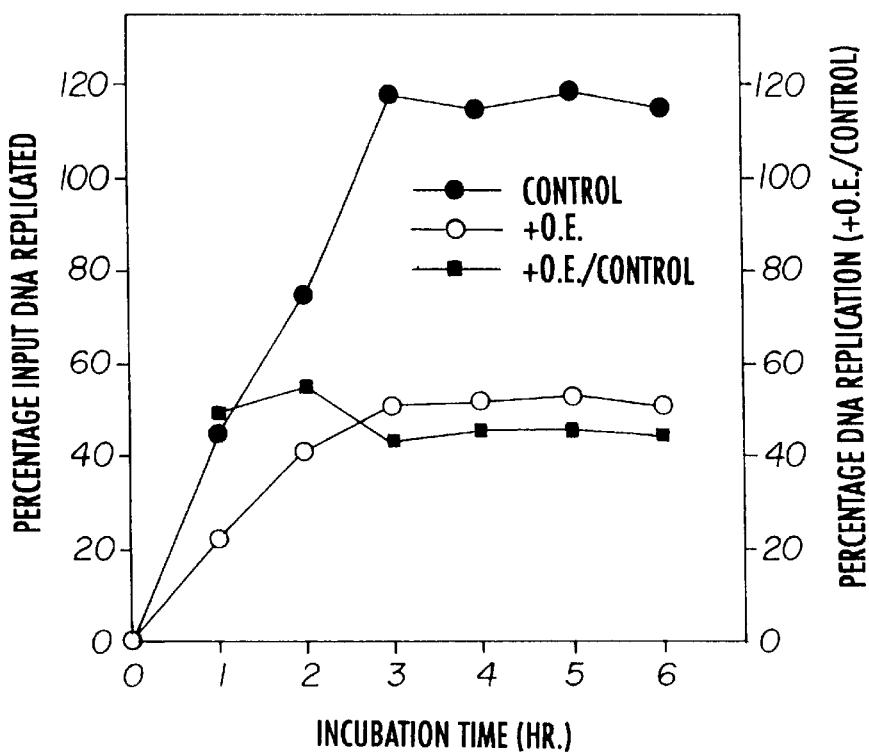
FIG. 4. Time course of DNA synthesis in egg extracts. Xenopus sperm nuclei were incubated in egg extract in the presence of extraction buffer (Control) or oocyte extract (+O.E.) for the indicated time. Percentage input DNA replicated and inhibition of DNA replication, expressed as percentage DNA replication (+O.E/Control), were determined as described in Example I.

To determine whether the decreased DNA synthesis observed above was simply due to a delay in the onset of DNA replication or due to the loss of replication capacity of egg extracts caused by addition of the oocyte extract, the time course of inhibition was examined. As shown in FIG. 4, DNA synthesis in the egg extracts was completed by 3 hours of incubation. It was estimated that 24.6 ng DNA was synthesized (117% of input DNA) by 3 hours. The calculation of greater than 100% replication probably resulted from slight over-estimation of the dATP pool size in egg extracts. Inhibition of DNA replication by the oocyte extract was observed at similar levels throughout 6 hours of incubation (FIG. 4).

In apparent contradiction with these results, Cox and Leno (*J. Cell Sci.*, 97, 177–184 (1990)) reported that a high speed extract of Xenopus oocytes did not inhibit DNA replication in cell-free extracts of Xenopus eggs. This discrepancy is probably the result of different methods used to prepare oocyte extracts. High speed (100,000×g, 1 hour) extracts of oocytes were used by Cox and Leno (*J. Cell Sci.,* 97, 177–184 (1990)), whereas low speed (16,00033 g, 2–10 minutes) extracts were used in this study. It seems likely that the inhibitors may have been depleted from the extracts prepared by the Cox and Leno, as were several putative nuclear pore proteins (L. S. Cox et al., *J. Cell Sci.,* 97, 177–184 (1990)).

Figure 5:
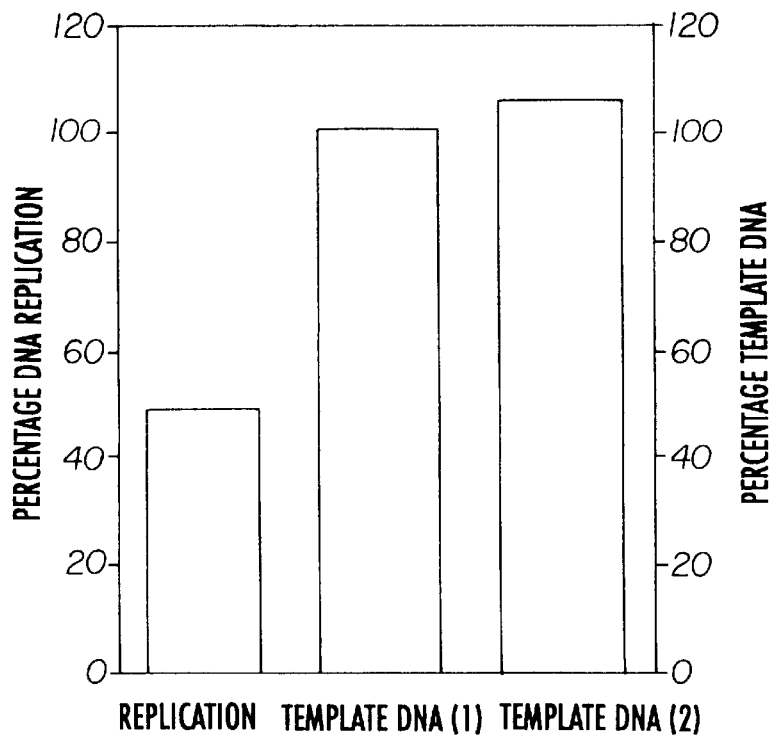
FIG. 5. Quantification of template DNA after incubation in cell-free egg extracts. [$^3$H]-labeled pXY65 DNA was incubated in egg extracts in the presence of extraction buffer or oocyte extract for 90 minutes. After incubation, [$^3$H]-DNA was quantified and percentage template DNA remaining was calculated as described in Example I. (1) and (2) refer to two different methods used for the quantification. For comparison, inhibition of replication of pXY65 DNA in the same egg extract, measured by [$^{32}$P] dAMP incorporation, is also shown.

2. Inhibition of DNA Replication in Cell-Free Egg Extracts by Oocyte Extracts Was Not Due to Template Degradation Since DNA molecules microinjected into oocyte cytoplasm are rapidly degraded (A. H. Wyllie et al., *Dev. Biol,* 64, 178–188 (1978)), inhibition of DNA replication by oocyte extracts could simply result from degradation of the template DNA. To test this, plasmid DNA template remaining after incubation in egg extracts in the presence of oocyte extracts was quantified. [$^3$H]-labeled plasmid pXY65 was not degraded in egg extracts to which oocyte extracts had been added when compared with control egg extracts (FIG. 5). Consistent with this, increased degradation of template DNA in egg extracts in the presence of oocyte extracts was also not detected by Southern blot hybridization analysis.

Figure 6A:
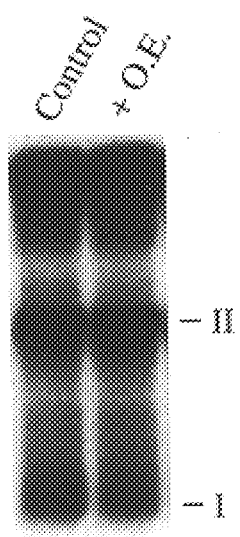
FIG. 6. DNA synthesis on single-stranded DNA templates in cell-free egg extracts: effect of oocyte extracts. (A) Single-stranded M13mp18 DNA was incubated in egg extracts in the presence of extraction buffer (Control) or oocyte extract (+O.E.) for 60 minutes. An autoradiogram of an agarose gel of reaction products after electrophoresis is shown. The positions of supercoiled (form I) and relaxed (form Ir—labeled as II in FIG. 6A) double-stranded M13mp18 DNA are indicated. (B) Single-stranded M13 or sperm nuclei were incubated in egg extracts in the presence of extraction buffer or oocyte extracts for 50 minutes (Experiments 1, 2 and 3) or 60 minutes (Experiments 4 and 5). Egg extracts were from five different preparations. The oocyte extract used in Experiments 1, 2 and 3 was from one preparation and the oocyte extracts used in Experiments 4 and 5 were from two other preparations.
Figure 6B:
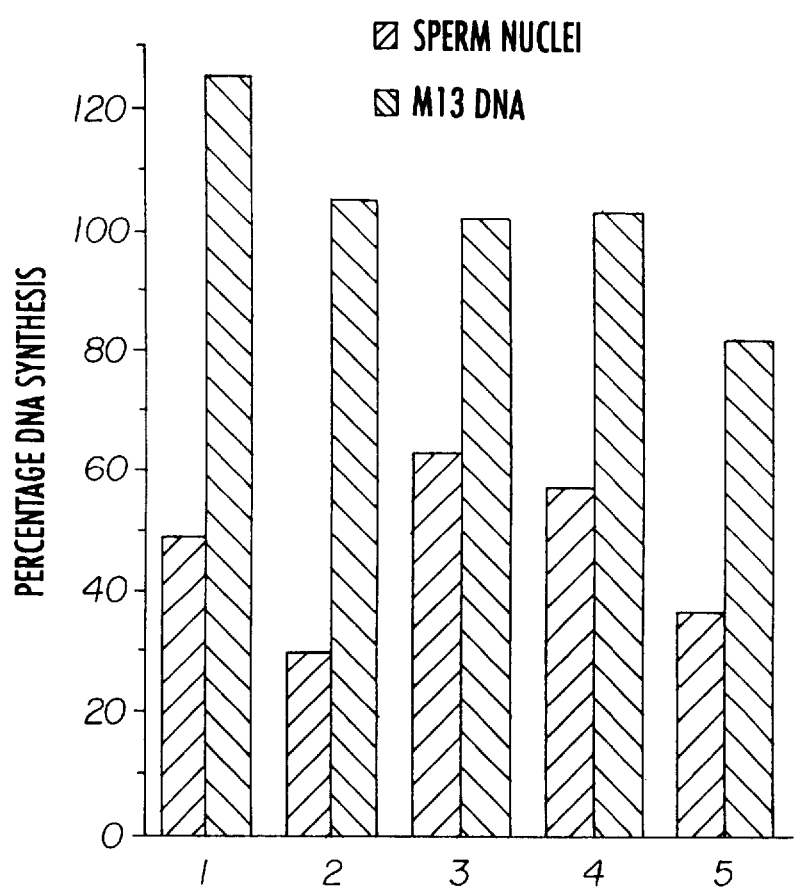

3. Complementary Strand DNA Synthesis on Single-Stranded DNA Templates in Cell-Free Egg Extracts Was Not Inhibited By Addition of Oocyte Extracts Oocyte extracts might inhibit DNA replication by either blocking events that lead to initiation of replication or by blocking nascent strand synthesis (chain elongation) on unwound DNA templates. The latter possibility is, a priori, unlikely since oocytes support DNA synthesis on microinjected single-stranded DNA templates (C. C. Ford et al., *Dev. Biol.* 43, 189–199 (1975); R. Cortese et al., *Proc. Natl. Acad. Sci. USA,* 77, 4147–4151 (1980)). As shown in FIG. 6, DNA synthesis on single-stranded DNA templates in cell-free egg extracts was not inhibited by oocyte extracts. This observation also supports the conclusion that inhibition of replication by oocyte extracts does not result from degradation of DNA templates.

Since DNA synthesis on single-stranded DNA templates was not inhibited by oocyte extracts, the inhibitors may specifically block a step leading to initiation of replication by mechanisms other than delaying the timing of initiation: even after incubation for as long as 6 hours (3 hours after completion of DNA synthesis in control egg extracts), inhibition was still observed at about same level. Other observations that the inhibitory factors in oocyte extracts were not removed by dialysis and were sensitive to heat treatment (FIG. 1A) suggest the inhibitors are macromolecules and probably proteins. Although the inhibitory factors are concentrated in the germinal vesicle, it is possible that one or more inhibitors are also present in the cytoplasm.

Figures 7A, 7B:
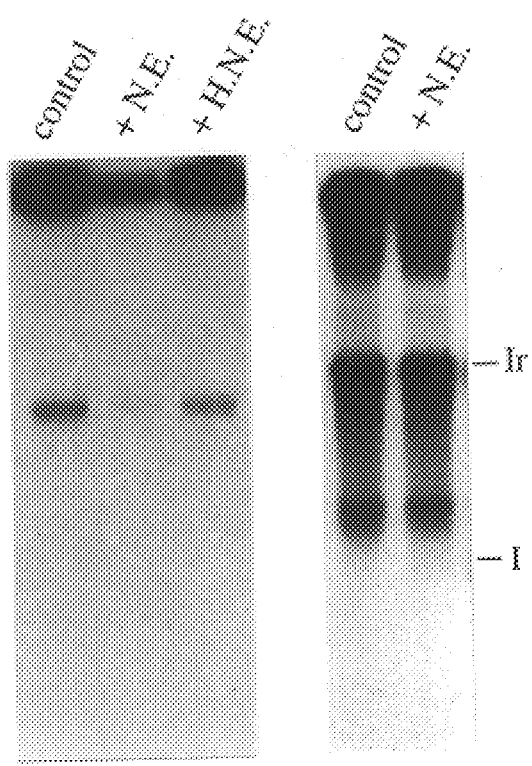
FIG. 7. Inhibition of replication of sperm nuclei by extracts of germinal vesicles. Sperm nuclei (A) or single-stranded M13mp18 DNA (B) were incubated in cell-free egg extracts in the presence of buffer J (control), oocyte nuclear extract (+N.E.) or heat treated (80° C., 10 minutes) oocyte nuclear extract (+H.N.E.) for 60 minutes.
Figure 9:
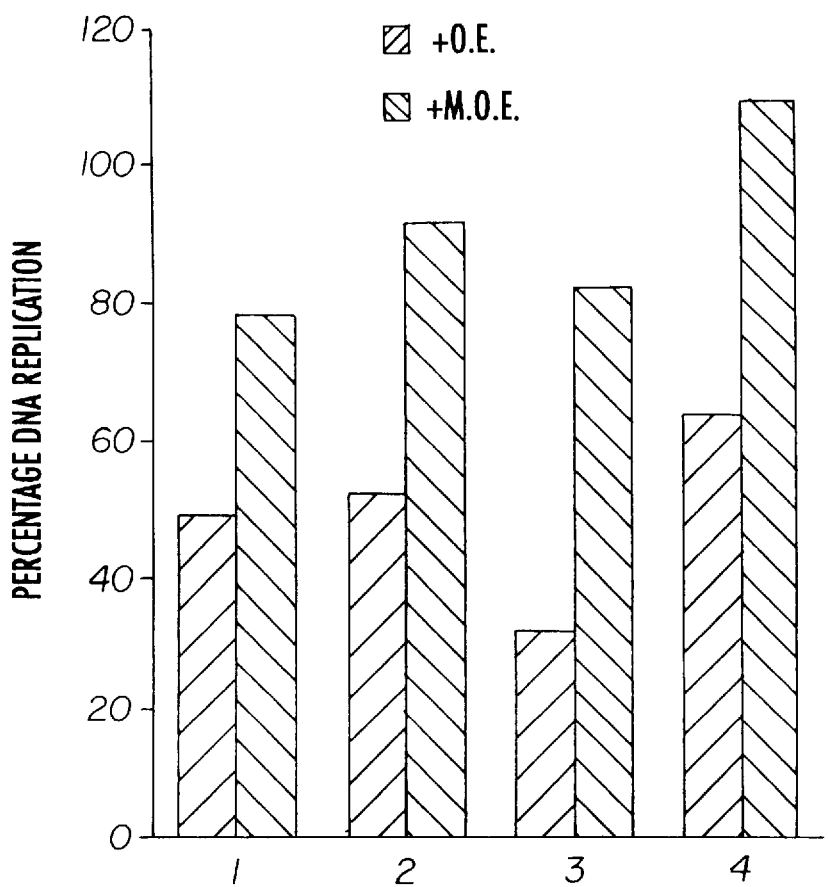

4. Extracts of Xenopus Oocyte Nuclei Also Inhibited DNA Replication in Cell-Free Egg Extracts If inhibitors play a physiological role in the regulation of chromosomal DNA replication, they are likely to be found in the nucleus. To examine whether the inhibitory factors are found in the oocyte nucleus, an extract from isolated Xenopus germinal vesicles was prepared and tested on DNA replication in egg extracts. Extracts of Xenopus germinal vesicles strongly inhibited replication of Xenopus sperm nuclei (FIG. 7A), but not complementary strand DNA synthesis on single-stranded DNA templates (FIG. 7B). The percentage inhibition of DNA replication by extracts of germinal vesicles was 8-fold higher than inhibition by whole oocyte extracts when compared on the basis of amount of proteins added to the egg extracts.

5. Oocyte Extracts Affected Nuclear Morphology of Xenopus Sperm Nuclei Formed in Cell-Free Egg Extracts Since nuclear assembly is a prerequisite for DNA replication in Xenopus egg extracts (see, e.g., L. S. Cox, *J. Cell Sci.,* 101, 43–53 (1992)), and since an extract of Xenopus oocytes did not support complete nuclear formation (L. S. Cox et al., *J. Cell Sci.,* 97, 177–184 (1990)), the effect of oocyte extracts on nuclear formation in egg extracts was examined. As shown in FIG. 8, the initial decondensation of Xenopus sperm chromatin in egg extracts was not affected by oocyte extracts (FIG. 8, 20 minutes). However, nuclei formed in the presence of oocyte extracts were much smaller than nuclei formed in egg extracts plus control buffer (FIG. 8, 50 minutes). These smaller nuclei, nevertheless, appeared to have complete nuclear envelopes (FIG. 8, 50 minutes).

Figure 9:
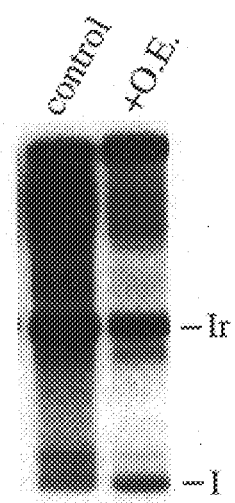
FIG. 9. Comparison of effect of extracts from immature (Stages I through V) versus mature oocytes (Stage IV) on DNA replication in cell-free egg extracts. Sperm nuclei were incubated in egg extracts in the presence of extraction buffer, extracts from immature oocytes (+O.E.) or extracts from mature oocytes (+M.O.E.) induced by either progesterone (1, 2) or by high pH solution (3, 4). Each experiment represents a different preparation of cell-free egg extract and oocyte extract. Protein concentrations of oocyte extracts or mature oocyte extracts were adjusted so that each experiment contained the same protein concentration.

6. Comparison of Inhibition of DNA Replication By Extracts Prepared From Immature Versus Mature Oocytes During Xenopus oocyte maturation, the germinal vesicle breaks down and the contents of the nucleus mix with the cytoplasm. Post-translational modifications of proteins occur actively during this period (See, e.g., J. Maller et al., *Dev. Biol.* 58, 295–312 (1977). To test the possibility that the inhibitor(s) of replication in oocyte extracts might be inactivated during oocyte maturation, the effect of extracts from oocytes matured in vitro on DNA replication in egg extracts were examined. Although extracts prepared from immature stage VI oocytes strongly inhibited DNA replication, extracts prepared by a similar method from oocytes matured in vitro by two different procedures showed much less, if any, inhibition of DNA replication in cell-free egg extracts (FIG. 9).

It should be pointed out that extracts prepared from mature oocytes sometimes showed inhibition of DNA replication in egg extracts, especially when higher concentrations of extracts were used and/or when replication activity of egg extracts was relatively low. The basis for this inhibition is not known, but could result from non-specific inhibition by high concentrations of proteins in the extracts or from incomplete inactivation of inhibitors during oocyte maturation. Nevertheless, even when extracts of mature oocytes resulted in inhibition, the inhibition was always much less than that caused by addition of extracts of immature oocytes.

EXAMPLE II

Isolation and Purification of the Inhibitor: the Türhüter Protein

Using inhibition of DNA replication in Xenopus egg extracts as an assay to monitor the presence of inhibitor in the progressive purification fractions (Example I), a nuclear matrix protein was purified to electrophoretic homogeneity from Xenopus ovaries.

Ovaries were prepared as described in J. Zhao et al. (*Biochemistry,* 32, 10622 (1993)). Adult *X. laevis* females were purchased from Xenopus I (Ann Arbor, Mich.). Ovaries (300 g) were removed from decapitated frogs and washed with modified Barth solution (Ford et al., *J. Embrol. Exp. Morphol.,* 37, 203–209 (1977)). All subsequent manipulations were carried out at 4° C. Ovaries were washed in a buffer containing 30 mM Tris-HCl, pH 8.5, 10 mM KCl, 5 mM MgCl$_2$, 1 mM EDTA, 1 mM DTT, 25% (v/v) glycerol, 0.5 mM PMSF, 1 mM benzamidine hydrochloride, and 0.5 mg/l leupeptin. Homogenenization, low-speed and high-speed centrifugation were preformed as described in Kaiserman and Benbow (*Nucleic Acids Res.,* 15, 10249–10265 (1987)). The high-speed supernatant was mixed with diethylaminoethyl (DEAE)-cellulose (600 ml)

equilibrated with Buffer A (Buffer A: 25 mM Tris-HCl, pH 8.0, 50 mM KCl, 5 mM $MgCl_2$, 1 mM ethylene diamine tetraacetic acid (EDTA), 1 mM dithiothreitol (DTT), 15% (v/v) glycerol, 0.5 mM phenylmethyl sulfonyl fluoride (PMSF), 1 mM benzamidine hydrochloride and 0.5 mg/l leupeptin) and stirred occasionally for 2.5 hours. The DEAE-cellulose resin and adsorbed material were packed into a column, and washed sequentially with 3 volumes each of Buffer A containing increasing concentrations of potassium chloride (200 mM, 300 mM and 500 mM KCl). The inhibitor was present in the 500 mM KCl fraction, which was concentrated using an Amicon ultrafiltration stirred cell fitted with a PM-10 membrane (Beverly, Mass.), dialyzed into Buffer B (Buffer B: 25 mM Tris-HCl (pH 7.5), 10 mM KCl, 1 mM EDTA, 1 mM DTT, 20% glycerol, 0.5 mM PMSF, 0.5 mM benzamidine hydrochloride, 0.5 mg/l leupeptin), and loaded onto a phosphocellulose column (20 ml) (Whatman Co., Hillsboro, Oreg.). The inhibitor was found in the flow-through and washes, and was concentrated with an Amicon (Beverly, Mass.) centriprep, dialyzed in Buffer C (Buffer C: 5 mM potassium phosphate, (pH 7.0), 10 mM KCl, 1 mM DTT, 15% glycerol, 0.25 mM PMSF, 0.2 mM benzamidine hydrochloride), and loaded onto a hydroxyapatite-agarose (HA-Ultrogel, IBS Biotechnics, Columbia, Md.) column (40 ml). The inhibitor in the flow-through and washes was concentrated, and loaded onto an Affigel Blue gel hydrophobic column (10 ml) (Biorad, Hercules, Calif.). The flow-through and washes, which contained the inhibitor, were concentrated and loaded onto an HA-ultragel column (50 ml) again. The flow-through and washes were concentrated, dialyzed into Buffer D (Buffer D: 10 mM Tris-HCl (pH 7.5), 50 mM NaCl, 0.2 mM EDTA, 1 mM DTT, 15% glycerol, 0.2 mM PMSF, 0.2 mM benzamidine hydrochloride), and loaded onto a Heparin-agarose column (15 ml) (Sigma Chemical Co., St. Louis, Mo.). After washing with 4 volumes of Buffer D, the column was eluted with 4 volumes of 0.2M, 0.5M, 1.5M, and 3M NaCl in Buffer E respectively. The inhibitor was found in 3M NaCl fraction. The NaCl concentration in the fraction was diluted to 0.5M, and the samples were concentrated and dialyzed in a buffer of 20 mM Tris-HCl (pH 7.5), 1 0 mM KCl, 0.2 mM EDTA, 1 mM DTT, 15% glycerol, 0.2 mM PMSF, and 0.2 mM benzamidine hydrochloride (Buffer F). The inhibitor concentration was estimated to be 1.2 $\mu$g/ml by comparing the intensity of the inhibitor band with bovine serum albumin band on a silver stained (using a silver stain kit, Biorad, Hercules, Calif.) SDS-PAGE gel (U. K. Laemmli, *Nature*, 227, 680 (1970)).

Analysis of the most purified fraction by sodium dodecyl sulfatepolyacrylamide gel electrophoresis (SDS-PAGE) revealed a band of molecular mass about 245 kDa (FIG. 10A). To confirm that the 245 KDA protein (p245) corresponds to the inhibitor, it was eluted from an SDS gel and renatured. Elution and renaturation of the inhibitor from SDS polyacrylamide gel were carried out as described in U. Laemmli, *Nature*, 227, 680 (1970) and J. Zhao et al, *Biochemistry*, 32, 10622 (1993). The position of the protein on the gel was determined by silver-staining (using a silver stain kit, Biorad, Hercules, Calif.) a lane of the same gel that contained the purified inhibitor. The renatured protein inhibited Xenopus sperm nuclear DNA replication and affected nuclear morphology exactly as did the most purified fraction.

Figure 10C:
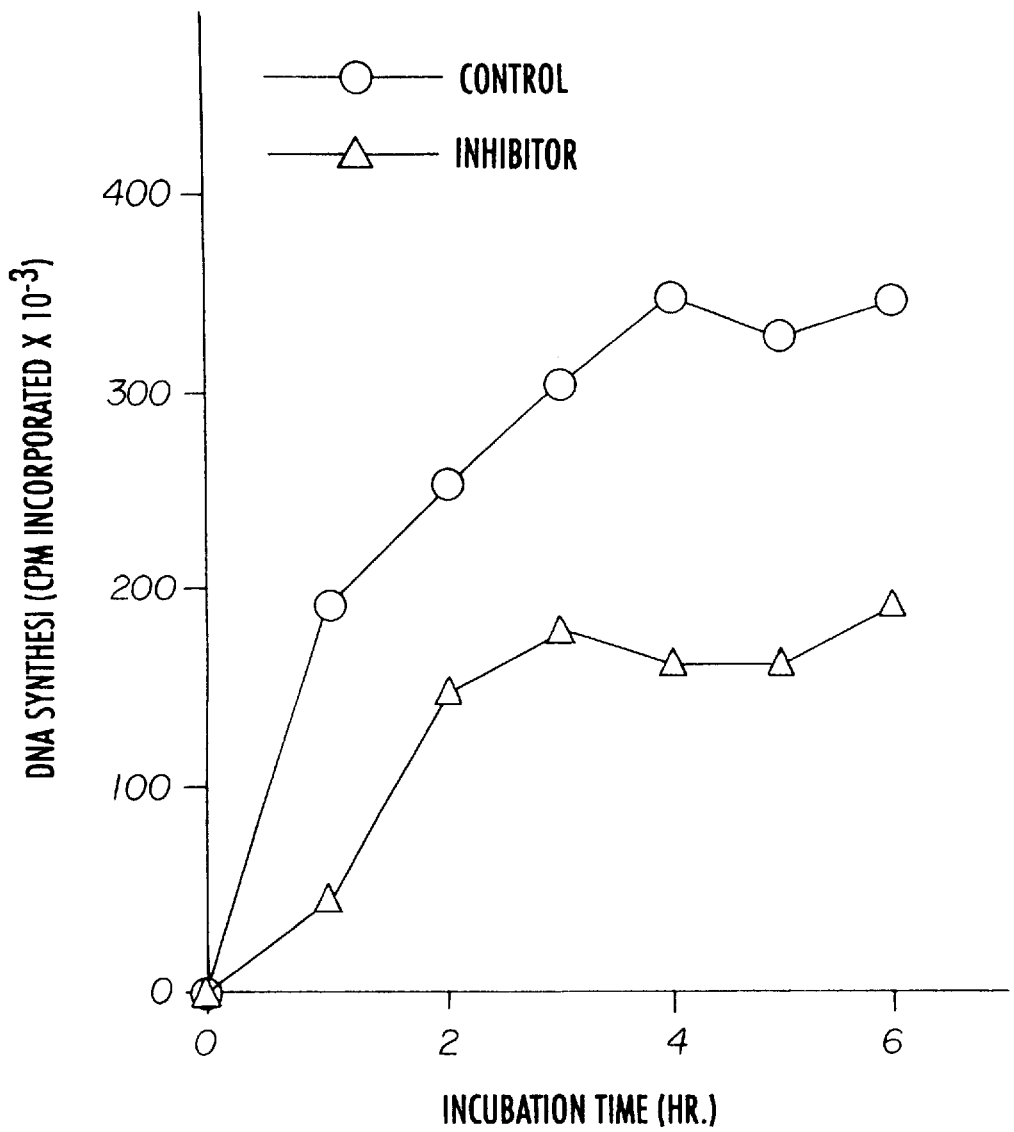
FIG. 10. A purified protein inhibits DNA replication in Xenopus egg extracts. (A) Silver-stained 5% SDS polyacrylamide gel of the purified inhibitor. SDS polyacrylamide gel electrophoresis was carried out according to U. Laemmli, Nature, 227, 680 (1970). The silver stain reagents were from Bio-Rad. The position of the protein on the gel is indicated. The molecular mass of the protein, estimated from molecular weight markers (Sigma and Novex) run on the same gel, is about 245 kDa. (B) Inhibition of DNA replication in Xenopus egg extracts by the purified protein. Demembranated Xenopus sperm nuclei were incubated in 35 µl egg extracts in the presence of control buffer (Control), the indicated amount (5 or 10 µl) of purified inhibitor (+Inhibitor), or heat treated (Δ, 80° C., 10 minutes) for 60 minutes. An autoradiogram of reaction products after electrophoresis in an agarose gel is shown. (C) Time course of DNA synthesis in the presence or absence of the most purified fraction. Xenopus sperm nuclei (4.5×10$^4$) were incubated in 40 µl egg extracts in the presence of 6 µl of the control buffer (Control) or 6 µl of the most purified fraction (Inhibitor) for the indicated time. In vitro DNA replication and quantification of DNA synthesis was carried out as described in the Examples and by J. Zhao et al., Dev. Biol., 164, 52 (1994). DNA synthesis is expressed as the total cpm incorporated into template DNA. All input DNA was replicated by 4 hours of incubation in the control extracts.

The purified protein completely blocked replication of Xenopus sperm nuclei in Xenopus egg extracts. Inhibition was heat sensitive (FIG. 10B). Complementary strand DNA synthesis on single-stranded DNA templates in egg extracts was not inhibited by the purified protein, suggesting that the inhibitor may block a step leading to initiation of DNA replication, rather than nascent strand synthesis on unwound DNA templates. This observation also indicated that inhibition of Xenopus sperm nuclear replication by the purified inhibitor was not the result of degradation of sperm nuclear DNA by the purified inhibitor. Time course experiments (FIG. 10C) showed that p245 blocked a step in DNA replication rather than just delayed onset of DNA replication, since replication was still inhibited by the most purified fraction even after 6 hours incubation. Preparation of demembranated Xenopus sperm nuclei and cell-free extracts of Xenopus eggs, in vitro reaction conditions, and analysis of reactions were as described in Example I. These results are consistent with those obtained with crude oocyte extracts (Example I).

Studies of in vitro DNA replication in Xenopus egg extracts have demonstrated that nuclear assembly is necessary for efficient DNA replication (See, e.g., J. J. Blow et al., *J. Cell Sci.* 95, 383 (1990)). It is known that Xenopus oocyte extracts, which inhibit DNA replication in Xenopus egg extracts, cause dramatic reduction in the size of nuclei formed in egg extracts (L. S. Cox et al., *J. Cell Sci.,* 97, 177–184 (1990)).

Figure 13A:
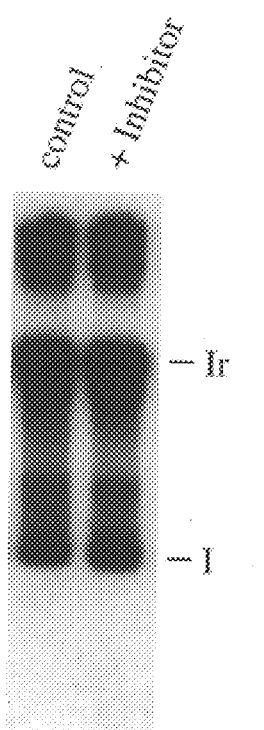
FIG. 13. (A) Effects of the purified protein on DNA synthesis on single-stranded DNA templates in egg extracts. Single-stranded M13mp18 (100 ng) was incubated in 35 $\mu$l egg extracts in the presence of 5 $\mu$l control buffer (Control) or 5 $\mu$l purified protein for 60 minutes. The control buffer was the buffer used for the most purified fraction, which is Buffer F described below in Example II. The positions of supercoiled (form I) and relaxed (form Ir) of monomeric double-stranded M13mp18 DNA are indicated. (B) Comparison of the effects of the most purified fraction on DNA synthesis of Xenopus sperm nuclei and plasmid DNA in egg extracts. (A) Xenopus sperm nuclei ($4.5 \times 10^4$) or plasmid pBR322 (133 ng) was incubated in 40 $\mu$l egg extracts in the presence of 6 $\mu$l control buffer (Control) or 6 $\mu$l of the most purified fraction for 4.5 hours. Inhibition of DNA replication (percentage DNA replication) was measured as described in the Examples and by J. Zhao et al., *Dev. Biol.*, 164, 52 (1994). (B) Xenopus sperm nuclei ($4 \times 10^4$) and pBR322 (133 ng) were mixed and incubated in egg extracts in the presence or absence of the most purified fraction as in (A). Incorporation of [$^{32}$P] dATP into high molecular weight Xenopus sperm chromosomal DNA and low molecular weight DNA between form I and form II of monomeric pBR322 were measured, respectively, and percentage DNA replication was calculated as described in the Examples and by J. Zhao et al., *Dev. Biol.*, 164, 52 (1994). 50 $\mu$g/ml cycloheximide was added to the egg extracts to arrest the egg extracts in S phase.
Figure 13B:
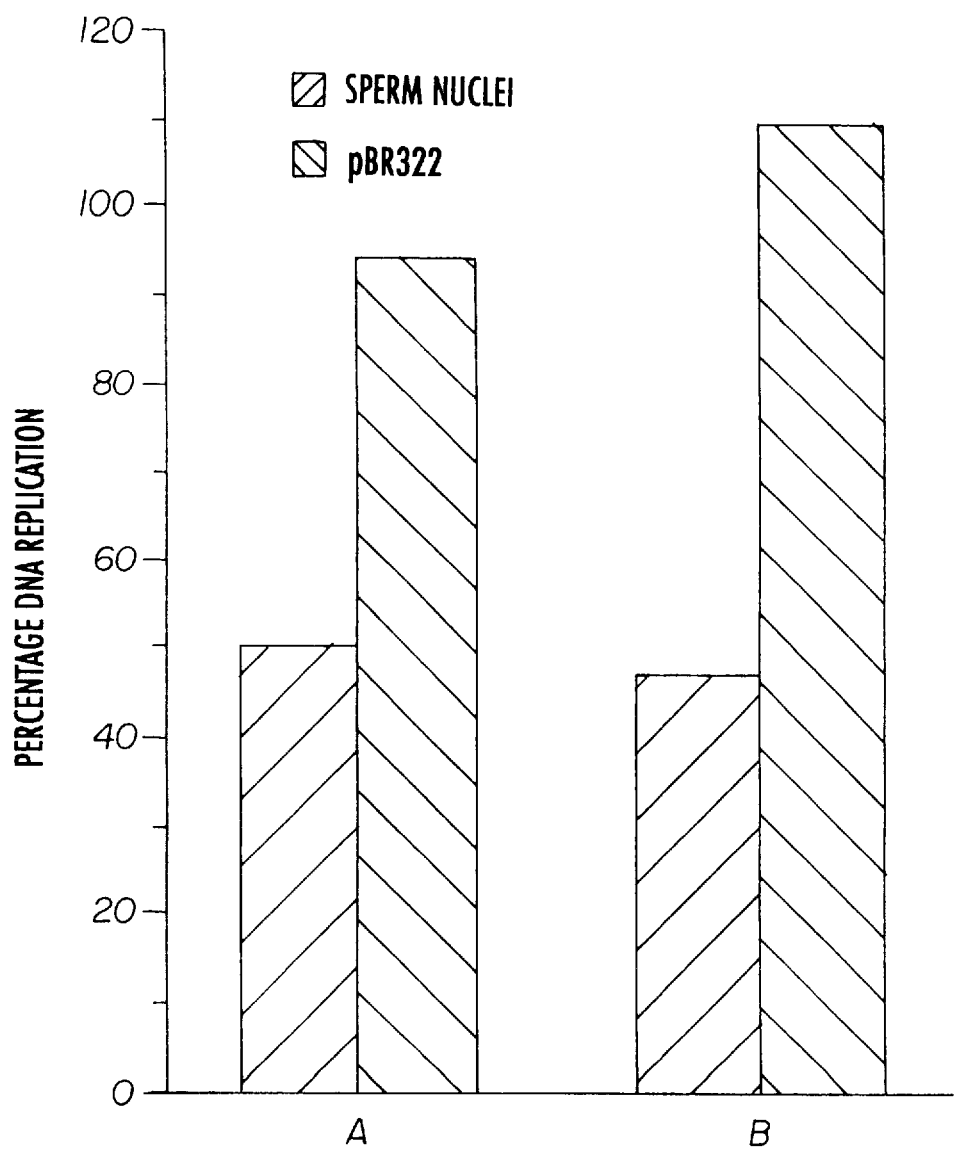

Although replication of Xenopus sperm nuclei was blocked, complementary strand DNA synthesis on single-stranded DNA templates in egg extracts was not inhibited by purified p245 (FIG. 13A), suggesting that the inhibitor may block a step leading to initiation of DNA replication, rather than nascent strand synthesis on unwound DNA templates. This observation also indicated that inhibition of Xenopus sperm nuclear DNA replication by p245 was not the result of degradation of sperm nuclear DNA caused by purified p245. However, replication of circular plasmid DNA in egg extracts was not inhibited by the most purified fraction (FIG. 13B) even when replication of Xenopus sperm nuclei was inhibited by more than 95%, suggesting that either specific DNA sequences or nuclear structure may be involved in the inhibition by p245.

To investigate this further, the effect of p245 on nuclear formation in egg extracts was examined. The most purified fraction did not affect initial chromatin decondensation of demembranated Xenopus sperm nuclei or nuclear envelope formation in egg extracts (FIG. 11, 20 minutes and 60 minutes). However, it prevented the nuclei from becoming swollen and caused alteration of the nuclear morphology as well as DNA staining pattern (FIG. 11, 60 minutes). The effect of the purified inhibitor on nuclear morphology was different from that of unfractionated oocyte extract. This might be because the effect of oocyte extracts results from combined effect of several factors in oocyte extracts.

If the inhibitor plays a physiological role in preventing DNA replication in the prolonged G2/prophase of meiosis I or between two successive meiotic divisions, the inhibitor might be inactivated or destroyed before, or at the time of, egg activation. To test this possibility, the effect of purified inhibitor protein on DNA synthesis in egg extracts released from metaphase arrest was examined. Xenopus egg extracts are arrested at metaphase by cytostatic factor (CSF) if they are prepared under conditions where $Ca^{2+}$ is sequestered. Metaphase extracts (CSF extracts) were prepared according to M. J. Lohka et al., *J. Cell Biol.,* 101, 518(1985) and A. W. Murray, *Methods in Cell Biol.,* 36, 581, (1991). Analysis and quantification of the reaction products were carried out as in Example I. The control buffer was the dialysis buffer, described above. Upon addition of exogenous $Ca^{2+}$, CSF is inactivatd and the extracts enter S phase. As shown in FIG.

12, the purified inhibitor did not block DNA replication in egg extracts released from metaphase arrest if the inhibitor was added to the metaphase extracts before the addition of Ca$^{2+}$. This result suggests that the inhibitor is inactivated by an activity in metaphase extracts or inactivated during the M phase to S phase transition. This suggests that a negative control mechanism is involved in the regulation of DNA replication in Xenopus meiotic divisions.

The 245 kDa protein, designated herein as the Türhüter protein, represses chromosomal DNA replication, probably by interfering with initiation, although the present invention is not dependent upon any particular theory of biological action of the Türhüter protein. Preliminary experiments show that inhibition requires genomic sequences; replication of plasmid pBR322 is not inhibited.

The complete disclosure of all patents, patent documents, and publications cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. An isolated protein having a molecular weight of about 245 kD as measured following electrophoresis on a sodium dodecyl sulfate-polyacrylamide gel, wherein the protein is isolated from homogenates of Xenopus ovaries and wherein the protein inhibits DNA replication in activated cell-free extracts of Xenopus eggs.

2. The protein of claim 1 wherein the protein inhibits double-stranded DNA replication.

3. A composition comprising the isolated protein of claim 1 and double-stranded DNA, wherein the isolated protein of claim 1 is capable of inhibiting replication of the double-stranded DNA.

4. A method of inhibiting double-stranded DNA replication comprising the step of:

adding the isolated protein of claim 1 to a solution comprising double stranded DNA.

5. A method for isolating a protein having a molecular weight of about 245 kD as measured by electrophoresis on a sodium dodecyl sulfate-polyacrylamide gel, comprising the steps of:

homogenizing Xenopus ovaries; and subjecting the homogenate of the homogenizing step to a series of chromatographic separations; and isolating a protein from the chromatographic separations wherein the protein has a molecular weight of about 245 kDa as measured following electrophoresis on a sodium dodecyl polyacrylamide gel and inhibits DNA replication in activated cell-free extracts of Xenopus eggs.

* * * * *